United States Patent [19]

Miller

[11] Patent Number: 4,495,105
[45] Date of Patent: Jan. 22, 1985

[54] PREPARATION OF HIGHER TIN CARBOXYLATES IN IMPROVED YIELDS USING AN INERT GAS

[75] Inventor: Richard F. Miller, Humble, Tex.

[73] Assignee: Atlantic Richfield Company, Los Angeles, Calif.

[21] Appl. No.: 473,836

[22] Filed: Mar. 9, 1983

[51] Int. Cl.³ .............................................. C07F 7/22
[52] U.S. Cl. .................................. 260/414; 260/429.7
[58] Field of Search .............................. 260/429.7, 414

[56] References Cited

U.S. PATENT DOCUMENTS 3,133,942  5/1964  Hahl ............................. 260/429.7 X
3,211,768 10/1965  Considine ..................... 260/429.7 X
3,546,263 12/1970  Ruf ..................................... 260/414

FOREIGN PATENT DOCUMENTS 1913284  7/1970  Fed. Rep. of Germany ...... 260/414

*Primary Examiner*—Helen M. S. Sneed
*Attorney, Agent, or Firm*—C. R. Reap

[57] ABSTRACT

Tin carboxylates of higher carboxylic acids can be prepared in high yields by:
(a) reacting either stannous oxide with an anhydride of a lower organic acid,
(b) reacting the product from (a) with at least one higher carboxylic acid, and
(c) recovering the tin carboxylate of said higher carboxylic acid.

13 Claims, No Drawings

PREPARATION OF HIGHER TIN CARBOXYLATES IN IMPROVED YIELDS USING AN INERT GAS

FIELD OF THE INVENTION

Catalysts used in cracking hydrocarbons can become contaminated and poisoned by accumulation in the catalyst of metal poisons such as nickel, vanadium, iron, copper and cobalt which are present in the hydrocarbon feedstocks. The detrimental effects of these metals can be mitigated and reversed by use of certain organo-tin compounds as metal passivators. Among those organo-tin compounds are tin carboxylates. The present invention is an improved method of preparing tin carboxylates in exceedingly high yields.

BACKGROUND OF THE INVENTION

Certain tin compounds are known to be used to treat those cracking catalysts conventionally employed in the catalytic cracking of hydrocarbons for the production of gasoline, motor fuel, blending components and light distillates. These conventional cracking catalysts generally contain silica, or silica-alumina. Such materials are frequently associated with zeolitic materials. These zeolitic materials can be used as naturally occurring, or they can be modified by conventional ion exchange methods to attach metallic ions which improve the activity of the catalyst.

While the presence on the catalyst of certain metals can be beneficial, the presence of others is detrimental. It is well known that varying amounts of metals such as nickel, vanadium and iron cause deterioration of the cracking catalyst during the cracking process. In fact, some oils contain these metals in such a high concentration that they cannot be economically catalytically cracked into gasoline and other fuels. The metals accumulate on the cracking catalyst and cause increased hydrogen production and coke laydown on the cracking catalyst, thereby adversely affecting the yield of desired products.

It has heretofore been proposed to passivate those deleterious metals by treating the contaminated catalyst with compounds containing antimony, tin, indium or bismuth (see U.S. Pat. No. 4,257,919). Tin compounds are particularly useful as passivating agents for vanadium. Among the organic tin compounds proposed are tin dicarboxylates such as tin didodecanoate, tin dioctadecanoate, tin tetradodecanoate and tin tetraoctadecanoate.

Prior art processes for tin carboxylate preparation involve direct reactions between tin hydroxides and carboxylic acids (see U.S. Pat. No. 2,684,973) or between alkyl tin oxides and acetic anhydride (see U.S. Pat. No. 2,838,554).

The production of tin carboxylates by the direct reaction between alkyl tin oxides and the desired higher carboxylic acids or acid anhydrides is generally less satisfactory for producing higher carboxylates because of the difficulty of the reaction and the low yield obtained. Accordingly, it is an object of the present invention to provide a process for preparation of higher carboxylates of tin which uses readily available reactants and affords high yields of the desired carboxylate. It is another object of the invention to provide a method of preparation wherein the tin carboxylate produced is substantially free of deletrious impurities and has a high level of thermal stability. These and other objects, aspects and advantages of the present invention will become apparent to those skilled in the art from the following description of the invention.

SUMMARY OF THE INVENTION

This invention relates to a highly effective and efficient method of preparing higher tin carboxylates in high yields comprising the steps of reacting tin oxide with an anhydride of a lower organic acid and reacting that reaction product with at least one higher carboxylic acid at a temperature sufficiently high to vaporize and remove volatile material. Optionally, a stream of an inert gas may be passed through the reaction mixture. The resulting product is the tin carboxylate of said higher carboxylic acid.

DETAILED DESCRIPTION

According to the present invention, higher tin carboxylates are produced from higher carboxylic acids by:

(a) reacting one or more tin oxides with an anhydride of a lower organic acid according to one or more of the following equations:

$$SnO + RCOOCOR \rightarrow (RCOO)_2Sn \quad (1)$$

$$SnO_2 + RCOOCOR \rightarrow (RCOO)_2SnO \quad (2)$$

$$SnO_2 + 2RCOOCOR \rightarrow (RCOO)_4Sn \quad (3)$$

wherein R is an alkyl group having up to 4 carbon atoms.

(b) reacting the product(s) from (a) with at least one higher carboxylic acid, preferably at temperatures sufficiently high to vaporize and expel volatile by-products of the reaction, according to one of the following equations:

$$(RCOO)_2Sn + 2R'COOH \rightarrow (R'COO)_2Sn + 2RCOOH \quad (4)$$

$$(RCOO)_2SnO + 2R'COOH \rightarrow (R'COO)_2Sn + 2RCOOH \quad (5)$$

$$(RCOO)_4Sn + 4R'COOH \rightarrow (R'COO)_4Sn + 4RCOOH \quad (6)$$

wherein R is as defined above and R' is an alkyl group having 5 to 24 or more carbon atoms; and (c) recovering the resulting tin dicarboxylate of said higher carboxylic acid.

The anhydrides of lower organic acids which are preferably employed in step (a) are those anhydrides which are commercially available or readily prepared. Such lower organic acid anhydrides include acetic anhydride, propionic anhydride, butyric anhydride, pentanoic anhydride and mixtures thereof. Acetic anhydride is the especially preferred anhydride of a lower organic acid.

In step (b) the reaction product from step (a) is reacted with one or more higher carboxylic acids, as indicated, to produce the products of the invention. Typical higher carboxylic acids are those acids which have at least six carbon atoms. There is no criticality on the upper limit for the number of carbon atoms. The upper limit is dictated only by practicality. Desirably, R' in the equation of step (b) is alkyl having from five to about 24 carbon atoms. Preferably, R' is a straight- or branched-chain alkyl having seven to eleven carbon atoms. Preferred higher carboxylic acids include the branched-chain carboxylic acids, such as the neodecanoic acids and 2-ethylhexanoic acid. Although R in the above reaction is depicted as a symmetrical anhydride it is understood that unsymetrical anhydrides may be used in the reaction, if desired. Furthermore, mixtures of anhydrides can be used, if desired. Similarly, in reactions 4, 5 and 6 the higher carboxylic acid component may be a simple carboxylic acid or a mixture of two or more carboxylic acids.

The reaction of step (a) can be conducted either with or without a solvent. When conducted with a solvent, the solvent should be inert to both the reactants and the reaction product. Suitable solvents include hydrocarbons having boiling points of at least 120° C., such as xylene, toluene, cumene, kerosene, and so forth.

Although elevated temperatures can be beneficially used to increase reaction speed, the temperature of the step (a) reaction is not critical. A typical temperature range is about 100° C. to 140° C. For examplification, when reacting the tin oxides with acetic anhydride at a temperature of about 120° C. the desired degree of conversion is obtained in about 3 to 4 hours.

As illustrated above by the equation of the step (b) reaction, the reaction by-product of step (b) is the lower organic acid or acids which correspond to the lower acid anhydride(s) employed in step (a). Thus when acetic anhydride is a reactant in step (a), acetic acid would be the by-product in step (b) when the higher carboxylic acid is reacted with the product of step (a). The lower organic acid by-product is desirably removed from the reaction environment in order to have the reaction equilibrium favor the formation of the tin carboxylate of the higher carboxylic acids. Removal of the by-product lower acid can be achieved by distillation at elevated temperatures, under reduced pressure or by a combination of these techniques.

The yield of the desired tin carboxylate of higher carboxylic acids can be further increased by passing an inert gas through the reaction mixture during the step (b) reaction. One method of passing the inert gas through the reaction mixture is by bubbling the gas through the reaction mixture using a subsurface sparge. The means used for passing the inert gas through the mixture is not critical and any means for gas-liquid contact can be suitably used. Inert gases useful in the invention are any gases which will not react with a component of the reaction mixture of step (b) and which will not leave a possibly deleterious residual substance in the tin carboxylate product. Suitable inert gases include nitrogen, argon, helium, and neon. Mixtures of inert gases can also be used. Nitrogen is the preferred inert gas.

The flow rate of inert gas is not critical and its magnitude is limited by practical considerations. For example, the volatile by-product of step (b) is generally removed by distillation, i.e., the vapors are condensed and removed. An excessive inert gas flow rate would overload the distillation condenser and thereby impede by-product removal as condensate. Furthermore, excessive flow rates could cause undesirable frothing of the reaction mixture. Suitable inert gas flow rates can easily be determined by those skilled in the art by balancing the gas flow rate against the physical effects to be avoided as a result of excessive flow. In general, gas flow rates of about 1 cu. ft./min. to about 20 cu. ft./min. are typical. Of course, ractor size and volume of the reaction mixture are also factors to be considered in determining an appropriate gas flow rate.

In carrying out the reaction of step (b), the higher carboxylic acid is mixed with the product of step (a) and the temperature of the mixture is increased until the by-product lower organic acid or acids are evolved as vapor. When acetic anhydride is a reactant in step (a), evolution of acetic acid vapor is observed in step (b) at a temperature of above about 150° C. The temperature is increased until the reaction is substantially complete, which will occur when the temperature reaches about 240° C. When the reaction of step (b) is substantially complete, it is advantageous to reduce the pressure of the reaction to effect as complete removal as possible of by-product lower organic acid and to effect the desired degree of reaction completion. Of course, it is possible to conduct step (b) entirely under a sub-atmospheric pressure in addition to the passage of an inert gas through the mixture. The Step (b) reaction pressure is not critical and its choice depends in part on the physical properties (e.g., boiling point) of the particular by-product species being removed. Thus, a convenient pressure can be easily determined by those having ordinary skill in the art.

The elevated temperature used to drive the reaction of step (b) to completion also serves to eliminate unreacted higher carboxylic acid, which is also vaporized. At the completion of the reaction of step (b), the principal product of the reaction of step (b), i.e, the product remaining in the reactor, is tin dicarboxylate essentially free of deleterious impurities. This product can be used as a hydrocarbon cracking catalyst passivator without further purification. Recovery of the product involves merely removing the tin dicarboxylate of the higher acid from the reactor after completion of step (b).

The following examples further illustrate specific embodiments of this invention but are not to be considered as limiting the invention to the specifics involved. Parts and percentages are on a weight basis unless otherwise indicated.

EXAMPLE I

A three neck reaction flask was equipped with a stirrer, a heating mantle and a reflux condenser attached to a Dean-Stark trap. The flask was charged with 270 grams of stannous oxide, 212 grams of acetic anhydride and 125 grams of xylene. With stirring, the reaction mixture was heated to 120° C. and maintained at that temperature for about 4 hours. Then, 368 grams of neodecanoic acid (technical grade) was added and the reaction mixture was heated to 195° C. During the heating, xylene was removed by distillation, and at approximately 155° C. acetic acid evolved and was removed. Heating was continued until the temperature of the reaction mixture reached about 195° C., at which point the reaction was terminated and the reactor contents cooled. The tin dineodecanoate yield was determined to be 82.6%.

The technical grade neodecanoic acid used is a product of Exxon Chemicals and is a highly branched multiisomer mixture combination with a typical hydrocarbon-type odor and melting point of less than −40° C. The structure of these isomers is generically represented by:

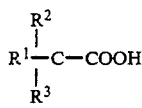

The sum of the carbon atoms for $R^1$, $R^2$ and $R^3$ in each isomer is eight. The Exxon technical grade neodecanoic acid employed has a typical isomer distribution as follows:

$R^1=CH_3$, $R^2=CH_3$, $R^3=C_6H_{13}$ ... 31%  (i)

$R^1<C_6H_{13}$, $R^2=CH_3$, $R^3>CH_3$ ... 67%  (ii)

$R^1<C_6H_{13}$, $R^2>CH_3$, $R^3>CH_3$ ... 2%  (iii)

Therefore, as the term is used herein, neodecanoic acid and neodecanoate esters include each of the several isomers of the technical grade material, either alone or in mixture.

EXAMPLE II

The apparatus described in Example I was charged with 270 grams of stannous oxide, 212 grams of acetic anhydride and 125 grams of xylene. With stirring the reaction mixture was heated to 120° C. and maintained at that temperature for about 4 hours. Then, about 368 grams of neodecanoic acid (technical grade) was added and the reaction mixture heated to 200° C. While heating the reaction mixture from 120° C. to 200° C., nitrogen was bubbled through the reaction mixture by means of a subsurface nitrogen sparge. During this period xylene was removed by distillation and acetic acid, which evolved at about 155° C., was also removed. When the temperature reached 200° C., the reaction mixture was cooled and the tin dineodecanoate yield was determined to be 89.2%.

EXAMPLE III

The procedure of Example II was repeated with the exception that the reaction mixture was heated to 225° C. after adding the neodecanoic acid reactant. Upon reaching 225° C., the reaction mixture was cold. The tin dineodecanoate yield was 92.2%.

EXAMPLE IV

The apparatus described in Example I was charged with 337.5 grams of stannous oxide, 265 grams of acetic anhydride and 100 grams of xylene. With stirring the reaction mixture was heated to 120° C. and maintained at that temperature for about 4 hours. Then, a mixture of 463 grams of neodecanoic acid (technical grade) and 362 grams of 2-ethyl hexanoic acid was added and the reaction mixture was heated to 240° C., during which period nitrogen was bubbled through the reaction mixture by means of a subsurface nitrogen sparge. While the reaction mixture was heated from 120° C. to 240° C., xylene and evolved acetic acid were removed by distillation. When the temperature reached 240° C., the reaction mixture was cooled. The yield of tin dicarboxylate was 220 grams. The percentage yield was 98.99%.

The foregoing examples illustrate the benefit obtained by the reaction of the invention. The reaction of Example I was carried out without the use of an inert gas atmosphere. The yield obtained was 82.6%. This compares very favorably with yields of product obtained by direct carboxylation of the tin oxide with higher carboxylic acids. When the reaction was carried out in a nitrogen atmosphere (Example II) a product yield of 89.2%, based on the theoretical yield, was obtained. In Example IV, in which the reaction was carried out under nitrogen and the higher acid component was a mixture of neodecanoic acid and 2-ethylhexanoic acid, the yield realized was 98.99%.

Although the invention is described with particular reference to specific examples, it is understood that alternate embodiments may be employed. For example, stannic oxide may be used in place of the stannous oxide. The scope of the invention is limited only by the breadth of the appended claims.

What is claimed is:

1. In a method of producing higher carboxylates of tin comprising the steps of:
   (a) reacting stannous oxide, stannic oxide or mixtures of these with an anhydride of a lower organic acid,
   (b) reacting the product from (a) with at least one higher carboxylic acid to produce a tin carboxylate of said higher carboxylic acid, and
   (c) recovering the tin carboxylate of said higher carboxylic acid,
the improvement comprising passing an inert gas through the reaction mixture during step (b).

2. The method according to claim 1 wherein the inert gas is selected from the group consisting of nitrogen, helium, neon, argon and mixtures of these.

3. The method according to claim 1 wherein the anhydride of a lower organic acid has the formula R—O—R' where R and R' are the same or different alkanoyl radicals having not more than five carbon atoms and said higher carboxylic acid has the formula R"COOH wherein R" is an alkyl radical having at least six carbon atoms.

4. The method according to claim 3 wherein said higher carboxylic acid is a mixture of at least two acids.

5. The method according to claim 4 wherein said higher carboxylic acid comprises a mixture of 2-ethylhexanoic acid and neodecanoic acid.

6. The method according to claim 1 wherein the reaction in step (b) is carried out at a temperature of about 150° C. to 300° C.

7. The method according to claim 1 wherein the anhydride of lower organic acid is acetic anhydride.

8. The method according to claim 8 wherein the volatile material removed comprises acetic acid.

9. The method according to claim 1 wherein step (a) is carried out in the presence of a solvent.

10. The method according to claim 9 wherein the solvent is a hydrocarbon having a boiling point of at least 120° C.

11. The method according to claim 9 wherein the solvent is selected from the group consisting of toluene, cumene, xylene and kerosene.

12. The method according to claim 3 wherein the higher carboxylic acid is 2-ethylhexanoic acid.

13. The method according to claim 3 wherein the higher carboxylic acid is neodecanoic acid.

* * * * *

UNITED STATES PATENT AND TRADEMARK OFFICE
CERTIFICATE OF CORRECTION

PATENT NO. : 4,495,105

DATED : January 22, 1985

INVENTOR(S) : Richard F. Miller

It is certified that error appears in the above-identified patent and that said Letters Patent is hereby corrected as shown below:

Claim 8, Column 6, Line 50

Number ---8---

Should be ---7---

Should read "according to claim 7"

Signed and Sealed this

Ninth Day of July 1985

[SEAL]

Attest:

Attesting Officer

DONALD J. QUIGG

Acting Commissioner of Patents and Trademarks